(12) United States Patent
Fini et al.

(10) Patent No.: US 10,022,482 B2
(45) Date of Patent: Jul. 17, 2018

(54) HEAT EXCHANGE DEVICE

(75) Inventors: Massimo Fini, Mirandola (IT); Reinhold Reiter, Crema (IT)

(73) Assignee: SIS-TER S.P.A., Palazzo Pignano (CR) (IT)

( * ) Notice: Subject to any disclaimer, the term of this patent is extended or adjusted under 35 U.S.C. 154(b) by 655 days.

(21) Appl. No.: 14/112,633

(22) PCT Filed: Jun. 5, 2012

(86) PCT No.: PCT/EP2012/060549
§ 371 (c)(1),
(2), (4) Date: Oct. 18, 2013

(87) PCT Pub. No.: WO2012/168211
PCT Pub. Date: Dec. 13, 2012

(65) Prior Publication Data
US 2014/0046248 A1  Feb. 13, 2014

(30) Foreign Application Priority Data
Jun. 9, 2011 (EP) .................................... 11425152

(51) Int. Cl.
| A61M 1/28 | (2006.01) |
| A61M 5/44 | (2006.01) |
| F28F 3/04 | (2006.01) |
| F24H 1/10 | (2006.01) |
| F28F 3/02 | (2006.01) |
| A61M 1/16 | (2006.01) |

(52) U.S. Cl.
CPC .............. *A61M 1/28* (2013.01); *A61M 1/166* (2014.02); *A61M 5/44* (2013.01); *F24H 1/102* (2013.01);
(Continued)

(58) Field of Classification Search
CPC .. A61M 1/28; A61M 5/44; A61M 2205/3653; A61M 2205/127;
(Continued)

(56) References Cited

U.S. PATENT DOCUMENTS 3,398,091 A  * 8/1968 Greatorex .............. B01D 53/22
                                                        159/1.1
6,743,201 B1   6/2004 Donig et al.
(Continued)

FOREIGN PATENT DOCUMENTS

EP         0956876      11/1999
GB         1592771      7/1981
(Continued)

*Primary Examiner* — Andrew Gilbert
*Assistant Examiner* — Hamza Darb
(74) *Attorney, Agent, or Firm* — Jacobson Holman, PLLC.

(57) ABSTRACT

A device to promote heat exchange to/from a medical liquid includes an inlet, an outlet, and a duct adapted to contain a flow of the medical liquid. The duct is enclosed between two walls, has a planar development defining a mean plane $\pi$, and has means for promoting turbulence in the flow of the medical liquid. At least one wall of the duct is suitable to allow a heat exchange with the flow of the medical liquid. The means for promoting turbulence has a plurality of fins, and each fin has a lenticular cross section and defines its own mean plane $\tau_n$ substantially perpendicular to plane $\pi$. A disposable cassette for use in a PD/APD treatment has a polymeric structure defining a first part, suitable for pumping and distributing the medical liquid, and a second part having the device to promote heat exchange.

24 Claims, 11 Drawing Sheets

(52) U.S. Cl.
CPC ............... *F28F 3/02* (2013.01); *F28F 3/048* (2013.01); *A61M 2205/127* (2013.01); *A61M 2205/366* (2013.01); *A61M 2205/3653* (2013.01)

(58) Field of Classification Search
CPC ...... A61M 2205/366; F28F 3/02; F28F 3/048; F24H 1/102
USPC .......................................... 392/465, 470–471
See application file for complete search history.

(56) References Cited

U.S. PATENT DOCUMENTS

| | | | |
|---|---|---|---|
| 7,153,285 B2 | 12/2006 | Lauman et al. | |
| 7,694,522 B2 * | 4/2010 | Nakae | F23R 3/002 60/752 |
| 8,803,044 B2 * | 8/2014 | Kienman | A61M 1/1696 219/607 |
| 2004/0150956 A1 * | 8/2004 | Conte | H01L 23/3677 361/709 |
| 2010/0329910 A1 | 12/2010 | Baumann et al. | |

FOREIGN PATENT DOCUMENTS

| | | |
|---|---|---|
| GB | 2251660 | 7/1992 |
| JP | H04159476 | 6/1992 |
| JP | 2001046495 | 2/2001 |
| JP | 2003206870 | 7/2003 |
| JP | 2007537390 | 12/2007 |
| WO | WO 2010/040819 | 4/2010 |

* cited by examiner

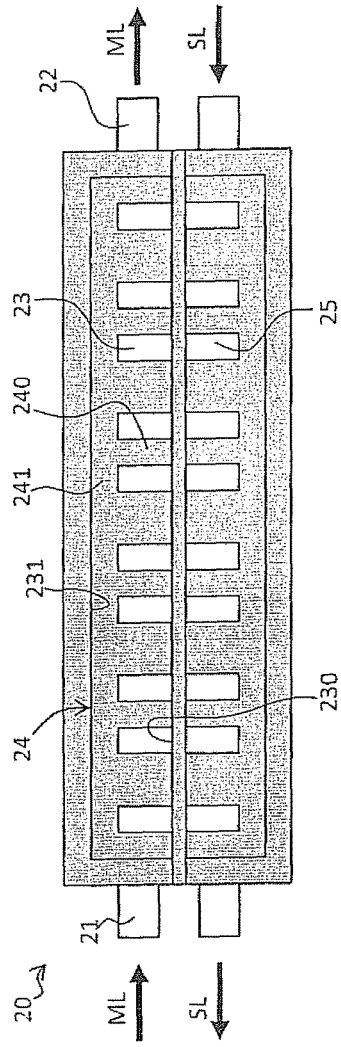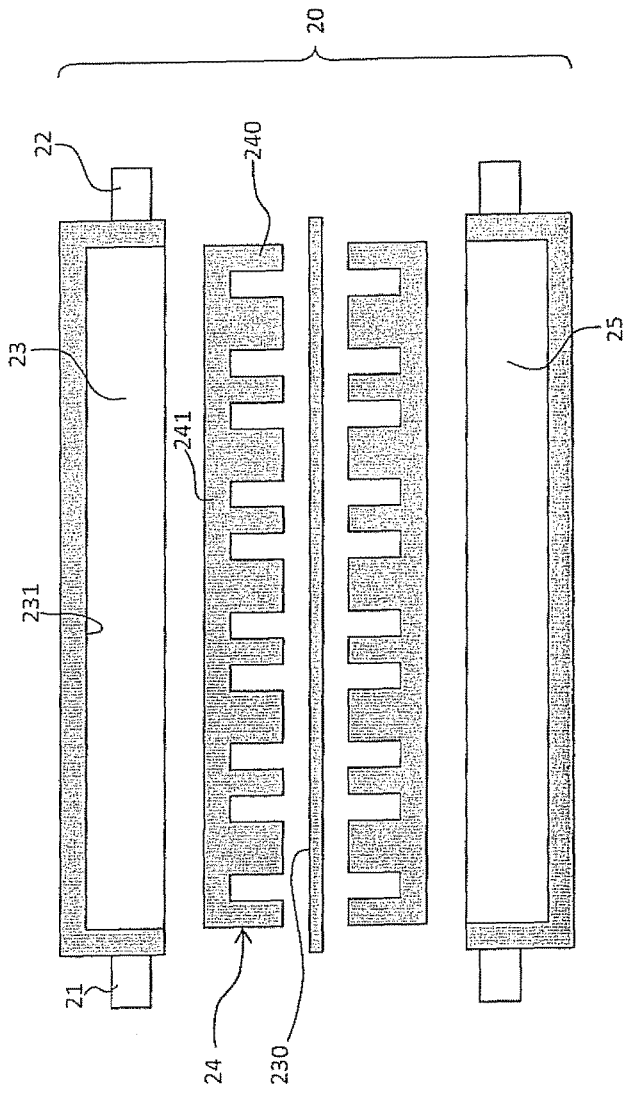
Fig. 1
Fig. 2

HEAT EXCHANGE DEVICE

CROSS-REFERENCE TO RELATED APPLICATIONS

This is a national stage of PCT/EP12/060549 filed Jun. 5, 2012 and published in English, which has a priority of European no. 11425152.3 filed Jun. 9, 2011, hereby incorporated by reference.

BACKGROUND OF THE INVENTION

1. Field of Invention

The invention relates to a device for heat exchange to/from a medical liquid, in particular for heat exchange between a thermally active plate and the liquid or between two different liquids. The invention relates moreover to a thermally active device suitable for use together with the disposable device.

The following description specifically relates to a disposable device for heating the dialysis liquid used in a peritoneal dialysis treatment. As the skilled person can immediately understand, this specific use of the invention is not to be considered in a restrictive manner, since the solution according to the invention can be profitably applied to other similar uses requiring a heat exchange to/from a medical liquid.

Accordingly, the wording "medical liquid" is understood as referring to any liquid which can be used in a medical treatment, for example a physiological liquid, a solution for dialysis (or dialysate), a solution for infusion, blood or a blood substitute, etc.

During therapeutic treatments which require the infusion of liquids into a patient and/or extracorporeal circulation it is required to constantly control the temperature of the liquid which is infused into the patient.

In the specific case of the peritoneal dialysis, a relatively large amount of dialysis liquid is infused in the peritoneal cavity of the patient. This process uses the patient's peritoneum in the abdomen as a dialyzing membrane through which substances to be removed from the blood (electrolytes, urea, glucose, albumin and other small molecules) diffuse in the dialysis liquid.

The temperature of the dialysis liquid before the infusion is usually quite lower than the body temperature. Depending on the storage conditions, the temperature of the dialysis liquid can be around 20-25° C. (room temperature) or even lower, e.g. around 4° C. (refrigerator temperature).

The infusion of a large amount of cold liquid into the peritoneal cavity, in the usual case, can cause a simple discomfort in the patient or, in the worst case, can entail the risk of inducing an undesirable state of hypothermia in the patient.

In view of the above, the dialysis liquid must be heated before infusion up to a temperature around 37° C. (body temperature).

2. Description of the Prior Art

Different solutions are known in order to heat the medical liquid before the peritoneal dialysis treatment.

According to a first solution disclosed in EP 0 956 876, a heat exchanger is provided in a multi function disposable cassette. According to such solution, in the heat exchanger area, the dialysis liquid is forced to flow along a duct which comprises a wall suitable to be heated by means of a heating plate. The duct has a winding overall arrangement, a tortuous development having a plurality of meanders and/or spirals. Such arrangement allows obtaining a relatively long heated path for the liquid in the relatively small heat exchange area available in the cassette.

According to a second solution disclosed in U.S. Pat. No. 7,153,285, a similar cassette is provided, and the liquid flowing therein is heated by a heating plate on one side and by an infrared lamp on the other side of the cassette.

The above devices, although widely used, are however not without of drawbacks.

The main defect of the known devices is the general low level of heat exchange efficiency. Both the known heat exchangers exploit the prolonged time during which the medical liquid is in contact with the heated wall of the duct, but they do not address the issue of improving the heat exchange efficiency.

Heat exchange must be performed in real time along the line used to convey the medical liquid. Poor efficiency means slowing down of the infusion operation. Moreover, where there is inefficient heat exchange, it is also required to use a notable temperature gradient in order to speed up the transfer of heat to the liquid. This may result in the presence of a heating plate(s) well above 80° C. which are extremely dangerous.

In fact, it may happen that the speed of infusion decreases and, consequently, the liquid remains inside the heat exchange device for longer than programmed. In such a case, a too high temperature of the heating plate could also easily raise the temperature of the liquid to a dangerous level. It can therefore be understood how a heat exchange device of this type is intrinsically dangerous and therefore requires a sophisticated system of sensors.

Moreover, a too high temperature of the heating plate could also damage the thin wall of the cassette which is intended to be heated.

SUMMARY OF THE INVENTION

The object of the present invention is therefore to solve at least partially the drawbacks identified in connection with the heat exchange devices of the known types.

An aim of the present invention is to provide a heat exchange device which has a high efficiency.

Moreover, the aim of the present invention is to provide a heat exchange device which has a simple design and low cost.

The abovementioned aims and object are achieved by a heat exchange device and by an assembly as described herein.

BRIEF DESCRIPTION OF THE DRAWINGS

The characteristic features and further advantages of the invention will emerge from the description provided hereinbelow, of a number of examples of embodiment, provided purely by way of a non-limiting example, with reference to the accompanying drawings in which:

FIG. 1 schematically shows a longitudinal cross sectional view of an embodiment of the heat exchange device according to the invention;

FIG. 2 schematically shows an exploded view of the cross section of FIG. 1;

DETAILED DESCRIPTION OF THE PREFERRED EMBODIMENTS

Figure 3:
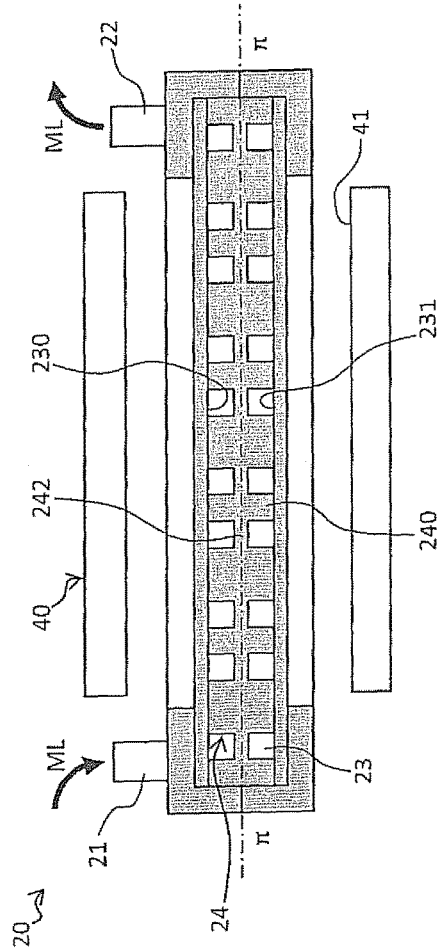
FIG. 3 schematically shows a longitudinal cross section of another embodiment of the heat exchange device according to the invention.
Figure 4:
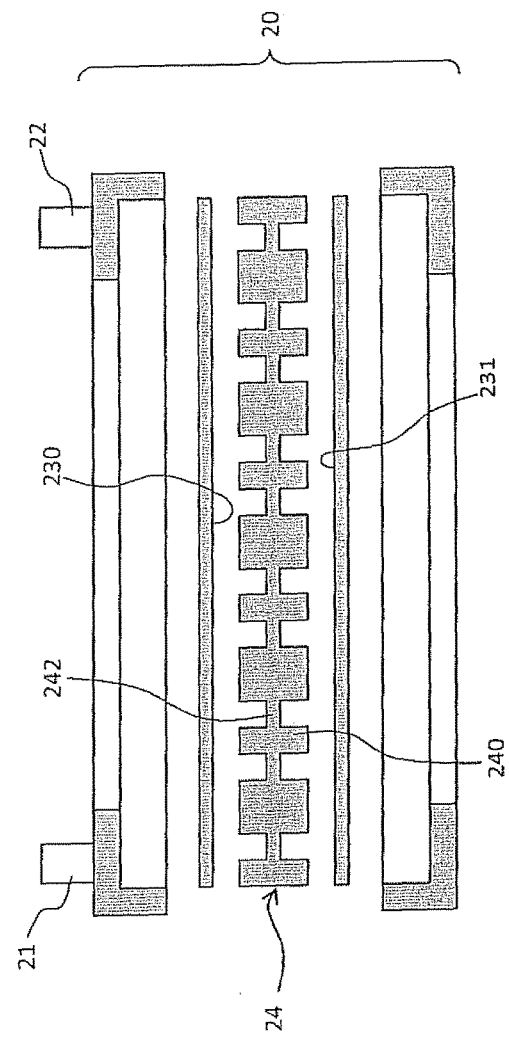
FIG. 4 schematically shows an exploded view of the cross section of FIG. 2.
Figure 5:
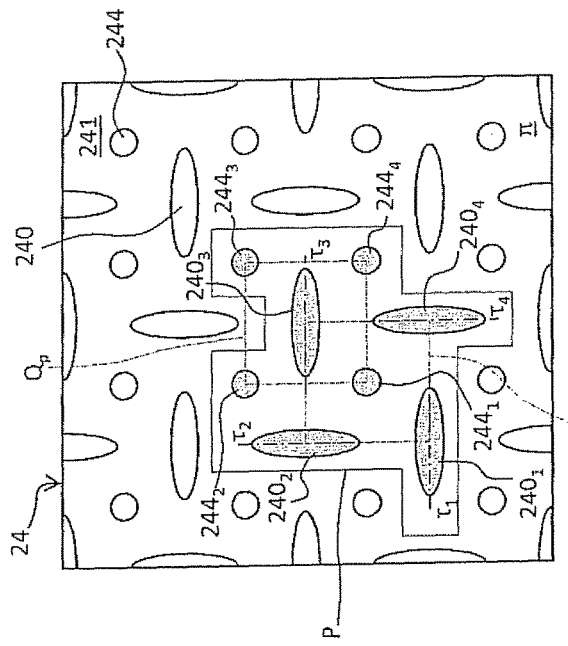
FIG. 5 schematically shows a plan view of the turbulence promoting means according to an embodiment of the invention.
Figure 6:
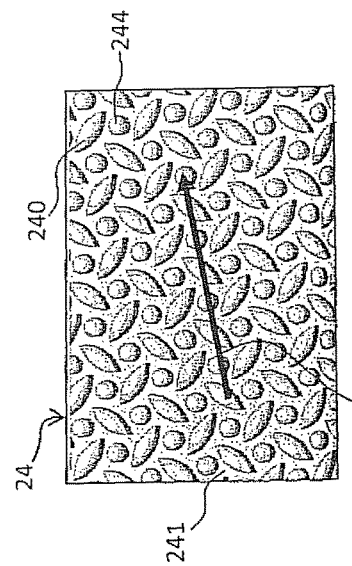
FIG. 6 schematically shows a plan view of means similar to those of FIG. 5.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention relates to a heat exchange device, indicated in its entirety by 20. The device 20 is designed to promote heat exchange to/from a medical liquid ML and comprises an inlet 21 adapted to receive the medical liquid ML, an outlet 22 adapted to release the medical liquid ML, and a duct 23 adapted to contain a flow of the medical liquid ML.

The duct 23 is enclosed between two walls 230, 231, has a planar development defining a mean plane $\pi$, and comprises means 24 for promoting turbulence in the flow of the medical liquid ML. At least one wall 230 of the duct 23 is suitable to allow a heat exchange with the flow of the medical liquid ML. The means 24 for promoting turbulence in the flow comprises a plurality of fins 240, wherein each fin $240_n$ has a lenticular cross section and defines its own mean plane $\tau_n$ substantially perpendicular to plane $\pi$.

In some embodiments of the device 20 according to the invention, the fins 240 are arranged according to a repeating pattern P comprising four fins $240_1$, $240_2$, $240_3$, $240_4$. A first pair of fins $240_1$, $240_3$ of the pattern P have their mean planes $\tau_1$, $\tau_3$ parallel to one another; a second pair of fins $240_2$, $240_4$ of the pattern P have their mean planes $\tau_2$, $\tau_4$ parallel to one another; and the mean planes $\tau_1$, $\tau_3$ of the first pair of fins $240_1$, $240_3$ are incident with the mean planes $\tau_2$, $\tau_4$ of the second pair of fins $240_2$, $240_4$.

Reference will be made below, in relation to the heat exchange device 20, to the concepts of "inner" and "outer". "Inner" is understood as referring to the parts of the device which, during use, are wetted by the liquid ML; on the other hand, "outer" refers to the parts of the device which, during use, are not wetted by the liquid ML.

Here and below the opening 21 will be regarded as an inlet and the opening 22 as an outlet. Obviously nothing would change if the functions of the two openings were assumed to be reversed. Preferably, the two walls 230 and 231 are sealed with respect to each other along their periphery so as to enclose the duct 23.

As reported above, the duct 23 of the device 20 has an overall planar development defining a mean plane $\pi$. In other words, with respect to an ordinary triplet of Cartesian axes, the extension of the duct 23 along two of such axes is considerably greater than its extension along the third axis. The former two axes define the mean plane $\pi$.

According to some embodiments of the invention, both the walls 230 and 231 are suitable to allow a heat exchange with the flow of the medical liquid ML flowing inside the duct.

The thermal exchange is obtained by means of thermally active means 40. According to some embodiments of the invention, the thermally active means 40 comprise at least one heating plate 41 which, in use, is suitable to come into contact with the outer side of the at least one wall 230 intended to allow the heat exchange with the medical liquid ML. According to some embodiments of the invention, for example the one shown in FIG. 3, the thermally active means 40 comprise two opposite heating plates 41, suitable to come into contact with the outer sides of both the walls 230 and 231.

At least one of the plates 41 is defined here as being thermally active. It is in fact able to assume a temperature different from the external temperature of the walls of the device 20. More specifically, according to certain embodiments, the thermally active plate 41 may assume higher temperatures so as to release heat to the contacting wall of the device 20. According to other embodiments, the thermally active plate 41 may assume lower temperatures so as to absorb heat from the contacting wall of the device 20. According to further other embodiments, the thermally active plate 41 may assume higher or alternatively lower temperatures so as to release or alternatively absorb heat to/from the contacting wall of the device 20. The temperature of the thermally active plate 41 can be preferably regulated via suitable regulating means.

The plate 41, depending on the different embodiments of the thermally active means 40, may comprise different means for rendering them thermally active. These means may consist of electric resistors which are designed to raise the temperature, or Peltier cells, which are able both to raise the temperature and, by reversing the polarity of the power supply, to lower it.

According to other embodiments, for example the one shown in FIG. 1, the thermally active means 40 comprise a further service duct 25, similar to duct 23. Both the two ducts 23 and 25 are comprised in the device 20 and are separated by the wall 230, which allows the heat exchange between them. While duct 23 is intended to contain the flow of the cold medical liquid ML which needs to receive a certain amount of heat, the service duct 25 is intended to contain the flow of another warm service liquid SL which is available for giving that amount of heat.

The two ducts 23 and 25 are preferably identical the one to the other, and more preferably they are mirror shaped with respect to the wall 230 which allows the heat exchange between them.

Figure 16:
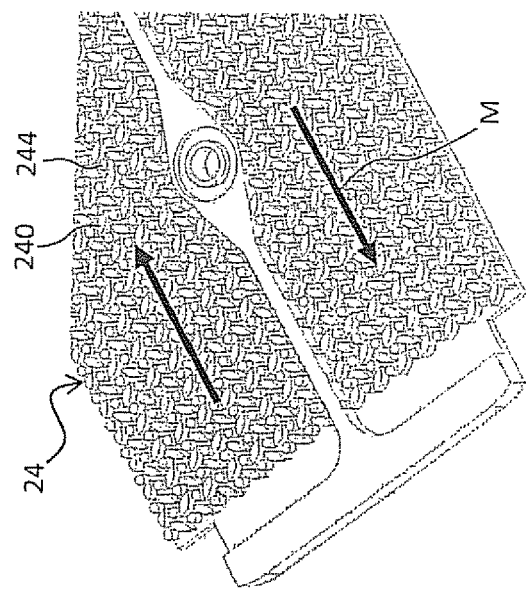
FIG. 16 schematically shows the detail indicated with XVI in FIG. 15.
Figure 15:
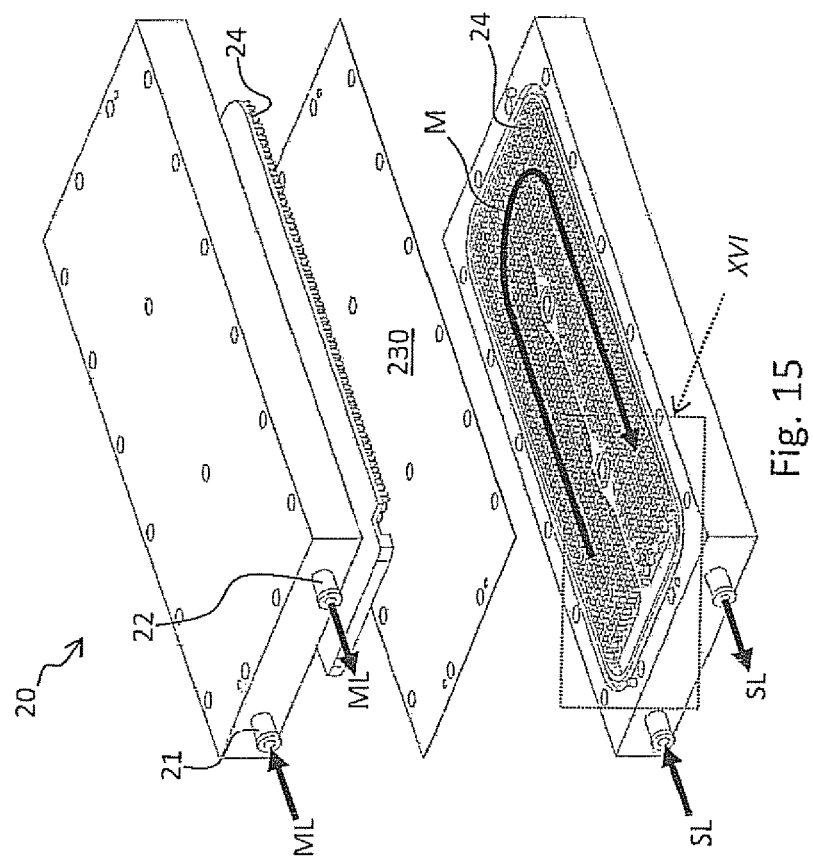
FIG. 15 schematically shows an exploded perspective view of another embodiment of the device according to the invention.

According to some embodiments, for example those shown in FIGS. 1 to 4 and 11 to 14, the inlet 21 and the outlet 22 are placed on opposite sides of the device 20. According to such embodiments, the overall liquid movement (represented in the figures by the arrow M) develops on plane π along a straight path. According to some other embodiments, for example the one shown in FIGS. 15 and 16, the inlet 21 and the outlet 22 are placed on the same side of the device 20. According to these embodiments, the two walls 230 and 231 are sealed with respect to each other not only along the periphery, but also partially along their centre line. Accordingly, the duct 23 and the overall liquid movement M develop on plane π along a U-shaped path.

It is to be considered here that the overall liquid movement M considered above is the final sum of all the micro diverging and re-converging movements imposed to the liquid flow by the turbulence promoting means 24. The effect of the turbulence promoting means 24 on the liquid flow is disclosed in detail below.

The wall 230, intended to allow the heat exchange, is preferably made from a material having a great thermal conductivity, e.g. such wall 230 can be made from metal materials like aluminium (Al), titanium (Ti) or stainless steel. The metal wall 230 can have a relatively great thickness (e.g. comprised between 0.1 mm and 0.4 mm).

Moreover, according to some embodiments, metal wall 230 could comprise a thin polymer lining should it be required to improve the biocompatibility thereof or other desirable characteristics such as the resistance to corrosion and/or to aggressive chemical agents.

Alternatively, the wall 230 can be made from a polymer, i.e. a material having a quite lower thermal conductivity. In the latter case, the polymeric wall 230 should have a thickness as thin as possible (e.g. comprised between 0.1 mm and 0.3 mm) in order to compensate for the material unfit properties. Obviously, from among the polymers suitable for contact with medical liquids, all other conditions being equal, it is preferable to choose a polymer with a relatively high thermal conductivity. According to certain embodiments, the thermal conductivity of the polymer may be increased by means of the addition of suitable fillers dispersed in the polymer itself. These fillers may be, for example, in a manner known per se, metal and/or ceramic particles.

According to some embodiments of the invention, for example those shown in FIGS. 1, 2, 5 to 9 and 14 to 16, the turbulence promoting means 24 comprise a continuous sheet 241 from which fins 240 protrude on one side only. Such embodiments of the turbulence promoting means 24 are intended to be used in connection with devices 20 where the duct 23 has only one thermal conducting wall 230. More specifically, as can be clearly seen in FIGS. 1 and 2, the sheet 241 is intended to be placed on the side of the duct 23 which is opposite the thermal conducting wall 230. According to this solution, the medical liquid ML mainly flows along the duct 23 between the thermal conducting wall 230 and the sheet 241.

According to some other embodiments of the invention, for example those shown in FIGS. 3, 4 and 10 to 13, the turbulence promoting means 24 comprise a discontinuous permeable sheet 242 from which fins 240 protrude on both sides. Such embodiments of the turbulence promoting means 24 are intended to be used in connection with devices 20 where the duct 23 has two thermal conducting walls 230 and 231. More specifically, as can be clearly seen in FIGS. 3 and 4, the permeable sheet 242 is intended to be placed in correspondence with the mean plane π of the duct 23. According to this solution, roughly half of the medical liquid ML flows between the wall 230 and the sheet 241, while the remaining liquid ML flows between the sheet 241 and the wall 231. Moreover the medical liquid ML, flowing along duct 23, continuously passes from one side to the other of the permeable sheet 242. According to some embodiments, the sheet 242 is rendered permeable due to a quantity of holes 245 distributed on the sheet 242. As already reported above, the turbulence promoting means 24 comprise a plurality of fins 240 which are arranged according to a repeating pattern P. The pattern P is here described in detail with specific reference to FIGS. 5, 7, 9 and 10.

In its basic configuration, the pattern P comprises four fins $240_1$, $240_2$, $240_3$ and $240_4$. A first pair of fins $240_1$, $240_3$ have their mean planes $\tau_1$, $\tau_3$ parallel to one another; a second pair of fins $240_2$, $240_4$ have their mean planes $\tau_2$, $\tau_4$ parallel to one another; and the mean planes $\tau_1$, $\tau_3$ of the first pair of fins $240_1$, $240_3$ are incident with the mean planes $\tau_2$, $\tau_4$ of the second pair of fins $240_2$, $240_4$.

According to some embodiments of the pattern P, the distance between the parallel planes $\tau_1$ and $\tau_3$ is equal to the distance between the parallel planes $\tau_2$, $\tau_4$.

According to some embodiments of the pattern P, the planes $\tau_1$ and $\tau_3$ are perpendicular to the planes $\tau_2$, $\tau_4$.

According to some embodiments of the pattern P, the intersections of the planes $\tau_1$, $\tau_2$, $\tau_3$ and $\tau_4$ with the plane π defines a quadrilateral $Q_f$. Quadrilateral $Q_f$ is preferably a rhomb and more preferably a square. Even more preferably, each fin 240 protrudes from its side of the quadrilateral $Q_f$ beyond the relative vertex.

According to some embodiments of the pattern P, the plane $\tau_1$ intersects the fin $240_4$, the plane $\tau_2$ intersects the fin $240_1$, the plane $\tau_3$ intersects the fin $240_2$ and the plane $\tau_4$ intersects the fin $240_3$. Preferably, the plane $\tau_1$ bisects the fin $240_4$, the plane $\tau_2$ bisects the fin $240_1$, the plane $\tau_3$ bisects the fin $240_2$ and the plane $\tau_4$ bisects the fin $240_3$.

Figure 7:
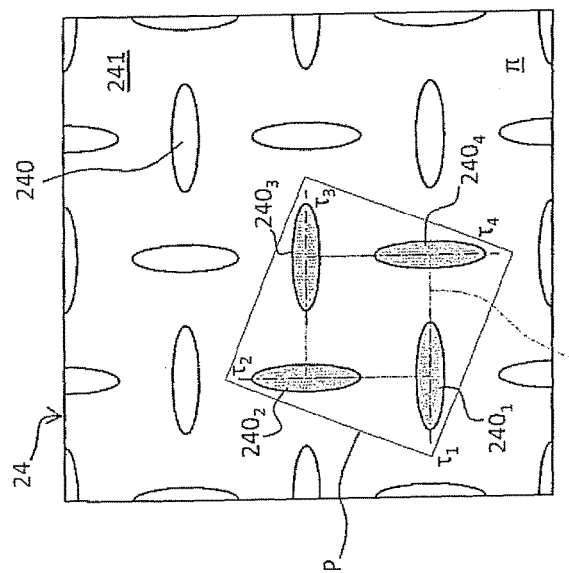
FIG. 7 schematically shows a plan view of the turbulence promoting means according to another embodiment of the invention.
Figure 8:
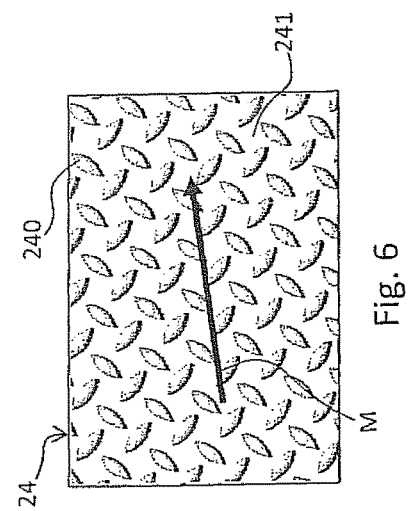
FIG. 8 schematically shows a plan view of means similar to those of FIG. 7.
Figure 10:
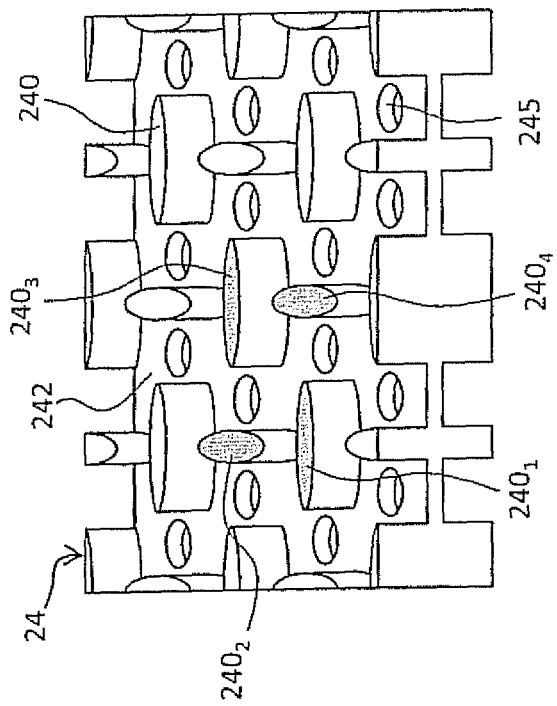
FIG. 10 schematically shows a perspective view of the turbulence promoting means according to another embodiment of the invention.
Figure 9:
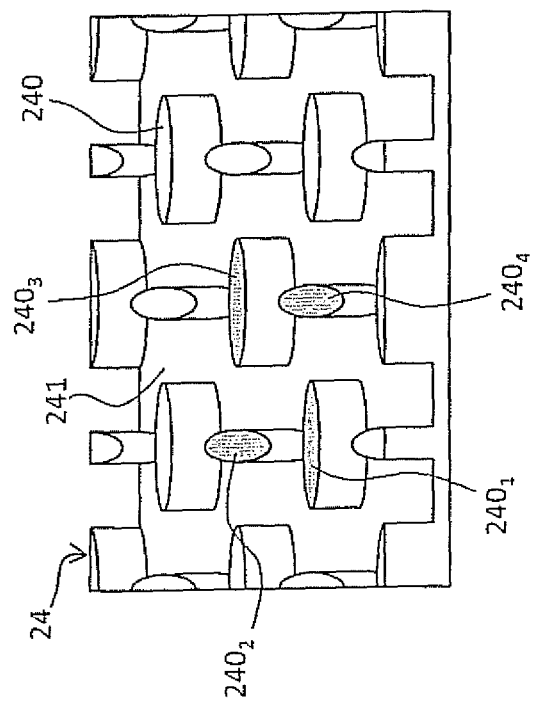
FIG. 9 schematically shows a perspective view of means similar to those of FIG. 5.
Figure 11:
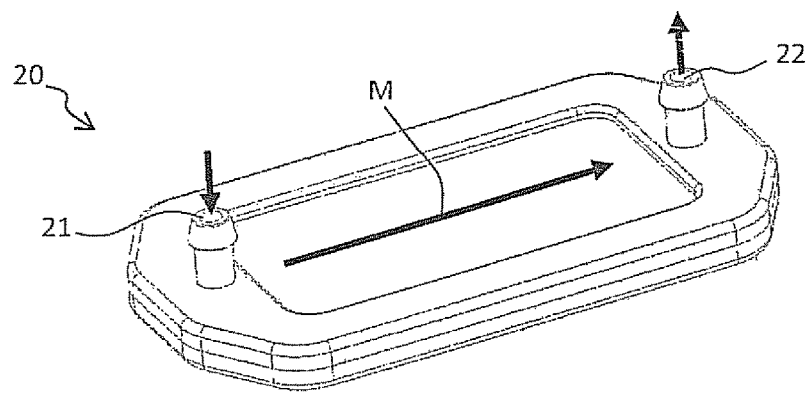
FIG. 11 shows a perspective view of another embodiment of the device according to the invention, similar to the one of FIGS. 3 and 4.
Figure 12:
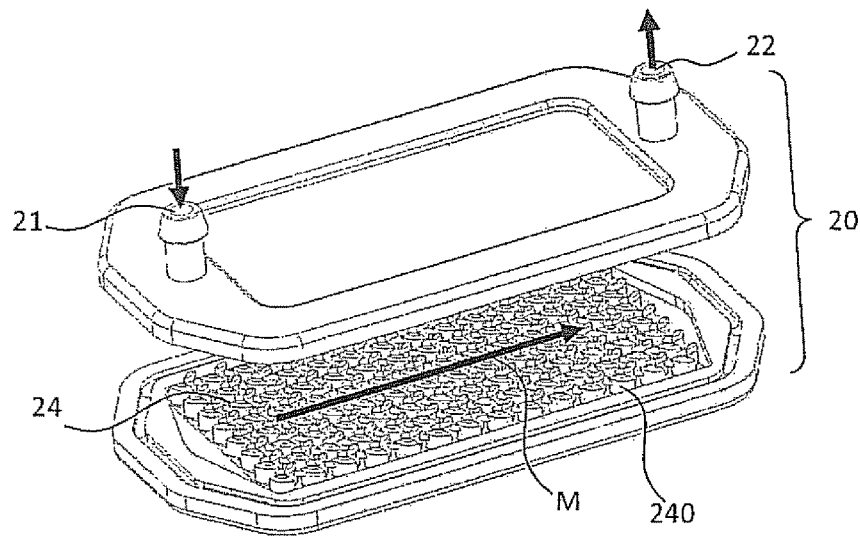
FIG. 12 shows an exploded perspective view of the device of FIG. 11.
Figure 13:
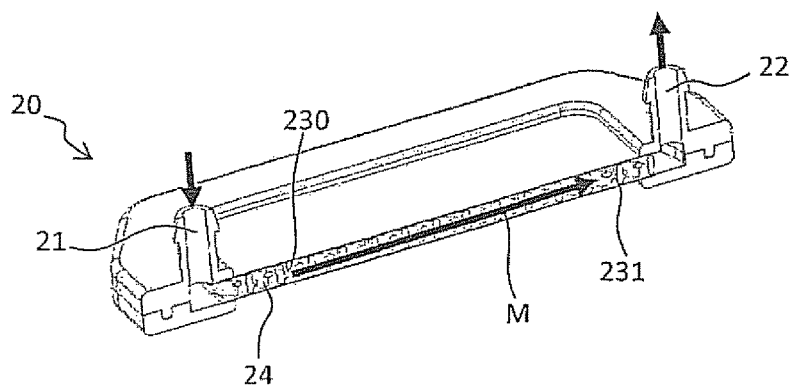
FIG. 13 shows a cross sectional perspective view of the device of FIG. 11.
Figure 14:
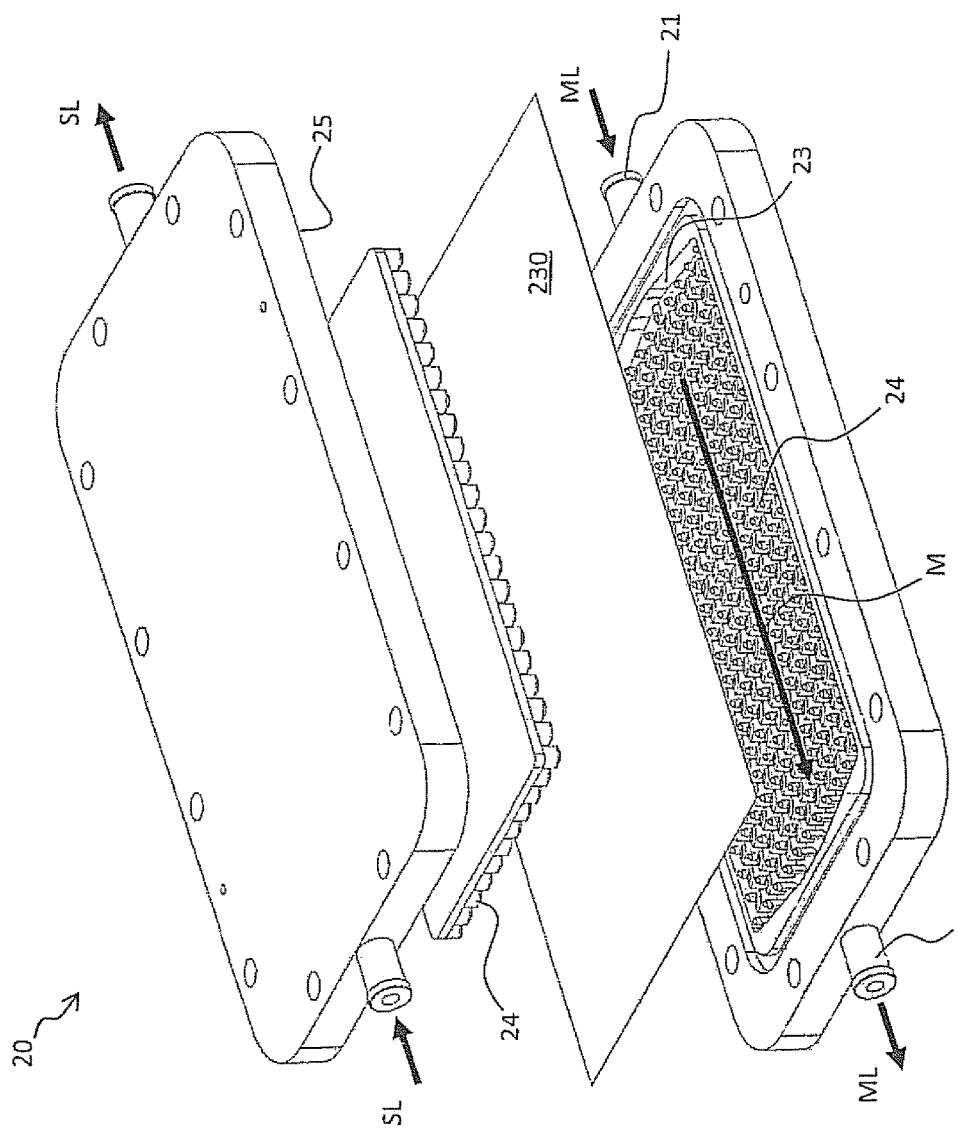
FIG. 14 shows an exploded perspective view of another embodiment of the device according to the invention, similar to the one of FIGS. 1 and 2.

According to some embodiments, for example those shown in FIGS. 7 and 8, the pattern P further comprise a plurality of pins 244, preferably four pins $244_1$, $244_2$, $244_3$ and $244_4$.

According to some embodiments of the pattern P, the four pins $244_1$, $244_2$, $244_3$ and $244_4$ are placed on the vertices of a quadrilateral $Q_p$, which is preferably identical to the quadrilateral $Q_f$ defined by the fins 240.

According to some embodiments of the pattern P, the quadrilateral $Q_p$ defined by the pins 244 is partly overlapping the quadrilateral $Q_f$ defined by the fins 240. Preferably, the quadrilateral $Q_p$ and the quadrilateral $Q_f$ overlap for a quarter of their surface.

According to some embodiments of the pattern P, the quadrilateral $Q_p$ surrounds one of the fins 240 and the quadrilateral $Q_f$ surrounds one of the pins 244.

According to some embodiments of the invention, the pattern P is so arranged in the duct 23 that the overall liquid movement M is parallel to one of the diagonals of the quadrilateral $Q_f$ defined by the fins 240.

According to some embodiments (not shown) the features of the turbulence promoting means 24 and of its pattern P of fins 240 may be defined solely along sections within the duct 23. In these embodiments, the fins 240 can be for example arranged in different homogeneous areas, each area having its own well defined pattern P. It has been noted, during specific tests carried out by the Applicant, that the transition between two adjacent homogeneous areas, results in substantial advantages in terms of mixing inside the flow.

Figure 18:
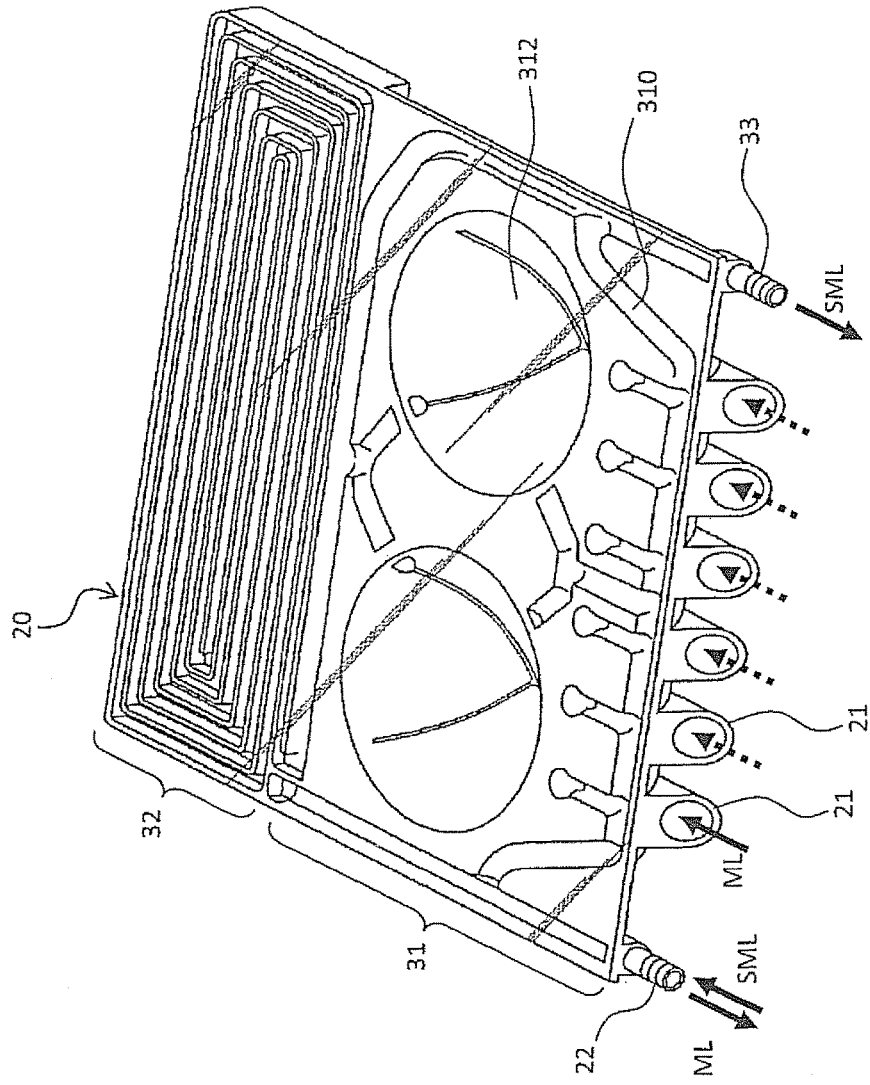
FIG. 18 shows a disposable cassette for Peritoneal Dialysis according to the prior art.

A specific embodiment of the heat exchanger 20 according to the invention will be described below with reference to FIGS. 18 to 20. Such particular embodiment is a incorporated in a cassette 30 for Peritoneal Dialysis (PD), specifically for Automated Peritoneal Dialysis (APD).

The cassette 30 of the known type and the Peritoneal Dialysis PD will be briefly described below, while a much more detailed description can be found in patent EP0956876 granted to the same applicant.

Peritoneal dialysis PD is a treatment for purifying the blood of a patient affected by renal insufficiency. Unlike conventional haemodialysis, in peritoneal dialysis the membrane used to filter the blood does not consist of an artificial element provided outside the patients body, but consists of the peritoneum. The peritoneum is a membrane situated in the abdomen and surrounding the internal organs. Since it is thin and highly vascularized it is possible to apply the physical principle of dialysis directly inside the patients body.

Peritoneal dialysis requires a catheter which must be introduced permanently inside the abdomen so as to allow connection of the peritoneal cavity to an external circuit. The external circuit generally comprises one or more bags containing pure dialysate and a drainage outlet. The dialysate represents, in this particular application, the medical liquid ML toward which the thermal exchange is provided.

The treatment of peritoneal dialysis generally comprises a first infusion phase (or fill) during which the pure dialysate ML is supplied via the catheter to the peritoneal cavity. During the second so-called dwell phase, during which no external operations are required, dialytic exchange between the patient's blood and the dialysate takes place. During the third and final drainage stage (or drain) the saturated dialysate SML is removed from the peritoneal cavity.

In order to obtain satisfactory purification of the blood, the entire treatment cycle described above must be repeated several times in succession over the course of 24 hours. In the case of APD, the various treatment cycles are performed in succession throughout the night by means of a special machine called an "automatic cycler" which automatically sets and regulates the fill, dwell and drain phases. The pure dialysate drawn from the bags needs to be heated up to body temperature before being infused in the peritoneal cavity of the patient, in order to avoid any risk of a thermal shock.

The cassette 30 according to the invention includes some important functions which are necessary for the APD treatment. The cassette is the disposable portion of the circuit which comes into contact with a potentially contaminated medical liquid SML, while the automatic cycler has to be necessarily reusable for many patients.

Cassette 30 comprises a structure of a rigid polymeric material which defines a first part 31, suitable for pumping and distributing the dialysate ML/SML, and a second part 32 suitable for providing a thermal exchange toward the dialysate ML. The first pumping and distributing part 31 is covered on its upper face by a thin and elastic polymeric film (shown by means of a light hatching in FIGS. 18 and 19). The second part 32 is covered by a thin and elastic polymeric film both on its upper and on its lower face. As can be seen in FIGS. 18 and 19, the cassette 30 comprises a plurality of inlets 21, each of them intended to be connected to an external bag of pure dialysate ML. Each inlet 21 is then connected, by means of an inner conduit network 310, to a pumping system 312. The pumping system 312 is then connected to the second part 32 which comprises a device 20 according to the invention. In particular, the device 20 is intended for providing a heat exchange to the dialysate ML, and comprises an inlet 21, an outlet 22, and a duct 23 adapted to contain a flow of the dialysate ML. The duct 23 is enclosed between the two polymeric films acting as the two walls 231, 232. The duct 23 has a planar development defining a mean plane $\pi$, and comprises means 24 for promoting turbulence in the flow of the dialysate ML, according to the invention.

Lastly the cassette 30 comprises an opening 22, which is intended to be connected to the peritoneal cavity of a patient, and an opening 33 which is intended to be connected to a drainage line.

Opening 22, once connected to the patient, represents the outlet for the pure dialysate ML which is delivered from the cassette 30 toward the peritoneal cavity of the patient during the fill phase. The same opening 22 represents the inlet for the saturated dialysate SML which is removed from the peritoneal cavity of the patient toward the cassette 30 during the drain phase and then is expelled through opening 33.

In the present description, attention is focused mainly on the flow of the cold pure dialysate ML which enters the cassette 30, is heated in the device 20 and then is infused in the peritoneal cavity of the patient. This is the reason why the opening 22 has been numbered and is considered in the following as the outlet of the device 20.

The automatic cycler, within which the cassette 30 is inserted during its operation, comprises a plurality of actuators suitable for pushing on the polymeric film which covers the cassette 30 so as to act as valves for the conduit network 310. In this manner the automatic cycler is able to select the pathways which are intended from time to time to house the dialysate flow.

As briefly described above, the embodiment of the cassette 30 according to the prior art, comprises a device 20 wherein a duct is provided having a tortuous development with a plurality of meanders and/or spirals. The dialysate ML goes along the upper spiral, then passes through a hole provided in the wall defining the mean plane $\pi$, and reaches another spiral on the lower side of the device 20. After having gone along the lower spiral, the dialysate ML exits the device 20 and, by means of the conduit network 310, reaches the outlet 22. The arrangement of the known spiral device 20 allows obtaining a relatively long heated path for the dialysate ML in the relatively small heat exchange area available in the cassette 30.

Figure 19:
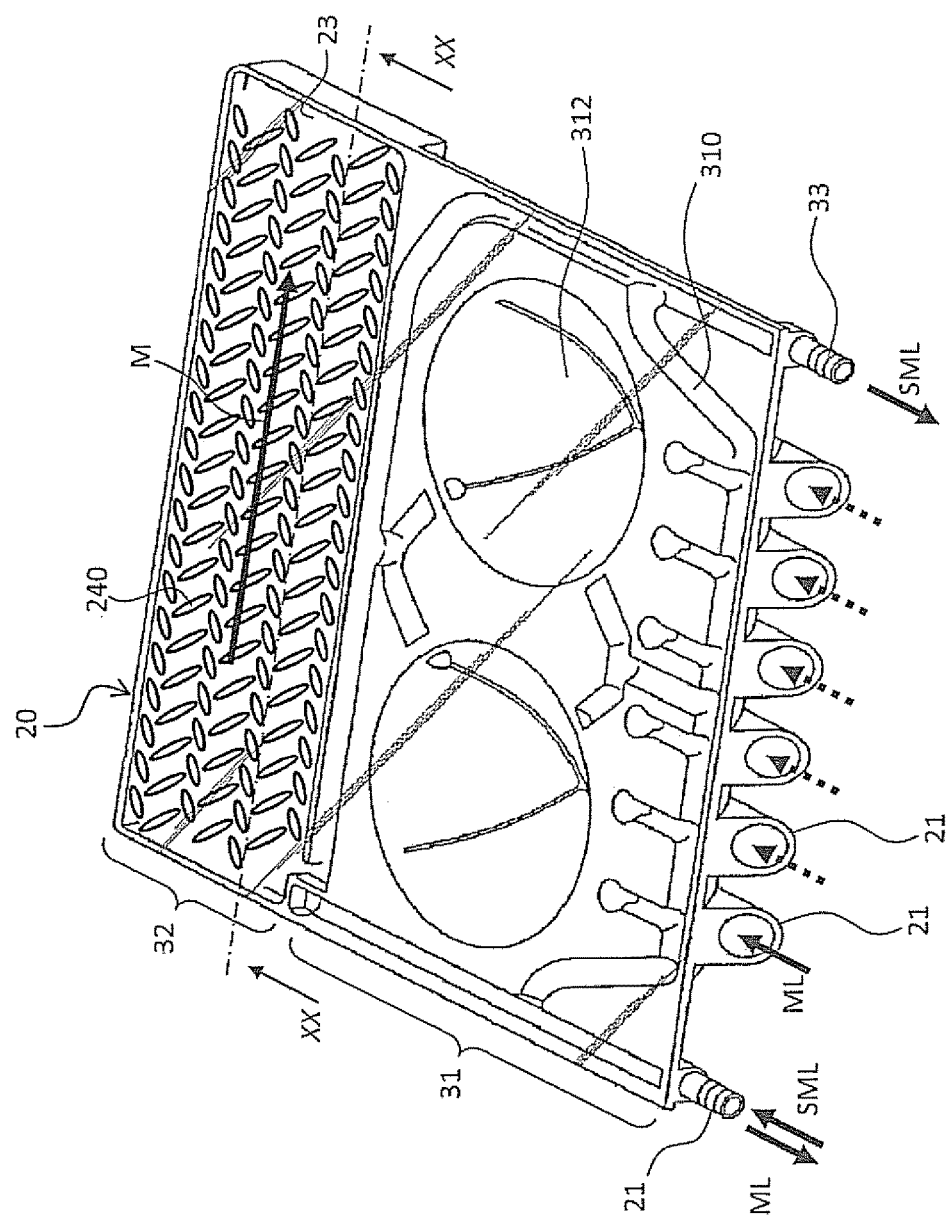
FIG. 19 shows a disposable cassette for Peritoneal Dialysis according to the invention.
Figure 20:
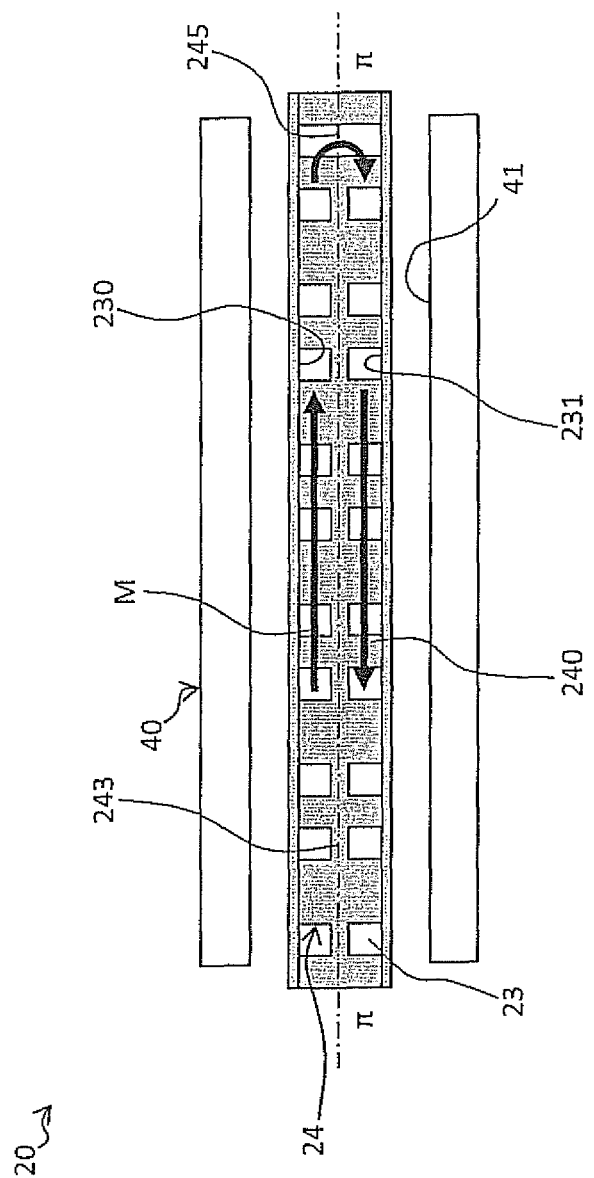
FIG. 20 schematically shows a cross section view taken along the plane indicated with XX in FIG. 19.

The improved embodiment of the cassette 30, shown in FIGS. 19 and 20, comprises a device 20 having a duct 23 according to the invention. The dialysate ML goes along the upper portion of the duct 23, then passes through a hole provided in the wall defining the mean plane $\pi$, and reaches another portion of the duct 23 on the lower side of the device 20. After having gone along the lower portion of the duct 23, the dialysate ML exits the device 20 and, by means of the conduit network 310, reaches the outlet 22.

In FIG. 20 a cross section of the device 20 is schematically shown. The cross section resembles the one of FIGS. 3 and 4, but in FIG. 20 the sheet 243 is not a permeable one, while in FIGS. 3 and 4 the sheet 242 is a permeable one. Some holes 245 are provided only at one end of the sheet 243 (right end in FIG. 20), thus allowing the dialysate ML to flow down to the lower portion of the duct 23 and so to flow back.

In FIG. 20 the thermally active means 40 are also shown, both the upper and the lower one, intended to provide heat to the dialysate ML.

As the person skilled in the art can understand, the various embodiments of the device 20 and/or the thermally active means 40 according to the invention have been described purely by way of example. In other words the different possibilities described above in terms of materials, overall form, pattern of the fins, etc., can be differently combined with each other also in ways which are not specifically described. For example, it is possible, without departing from the scope of the present invention, to form a U-shaped duct 23 (similar to the one of FIGS. 15 and 16) with two thermally active walls 230, 231 and permeable turbulence promoting means 24 (similar to the one of FIGS. 3, 4 and 11 to 13).

As the person skilled in the art can understand from the above description, the particular internal configuration of the device 20 according to the invention is able to achieve a high heat exchange efficiency. The planar arrangement of the duct 23 obtains a flow of liquid ML having a minimum thickness. The minimum thickness of the flow allows minimization of the thermal boundary layer effect, this effect resulting in large temperature differences between the layer of liquid directly in contact with the wall and the layers situated within the flow and at a distance from the wall. The thermal boundary layer effect thus results in the need, in low-efficiency exchangers of known type, for high wall temperatures (80-90° C.) in order to compensate for the difficulty in supplying heat to the deep layers within the flow. As already mentioned in the introduction, these wall temperatures are inherently dangerous for the patient's health and, in any case, for the exchanger itself.

Furthermore, the arrangement of the fins 240 along the duct 23 induces a high turbulence which ensures intense mixing in the flow. Intense mixing further limits the boundary layer effect in the liquid ML. The liquid which is in direct contact with the thermally active wall along a duct section, because of the intense mixing, will almost certainly be situated at a distance from that wall along a subsequent duct section. In other words, the high degree of mixing or turbulence phenomena induced in the flow by the particular configuration of the channel network continuously mixes the liquid ML, preventing the possible formation of large temperature differences within it.

Figure 17:
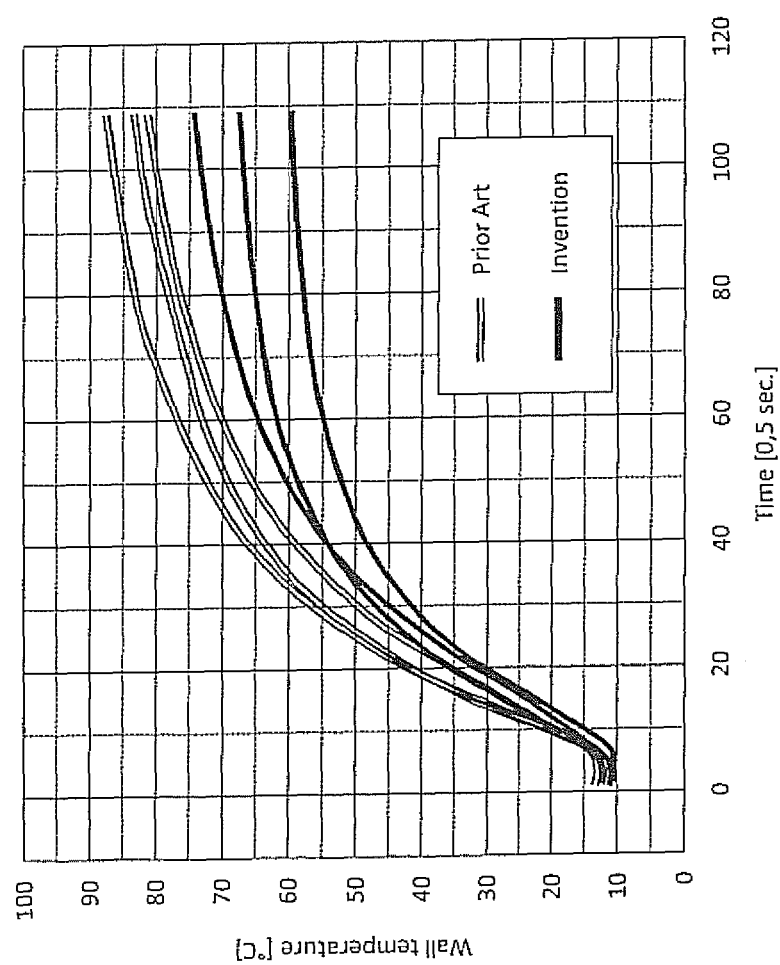
FIG. 17 schematically shows in form of a diagram the results of some comparison tests conducted on the devices according to the prior art and according to the invention.

The significant reduction in the boundary layer effect results in a considerable increase in the heat exchange efficiency in the circuit according to the invention compared to known types of circuits. Because of the high heat exchange efficiency it is thus possible to keep the wall temperature within values which are highly acceptable in terms of the patient's safety (60-75° C., depending on the materials used). The reduction in the wall temperature allowed by the invention is well appreciable from the diagram of FIG. 17. Such diagram schematically shows the results of some tests conducted on the devices according to the prior art in comparison with the devices according to the invention. As the skilled person can easily appreciate, the devices according to the invention permit to maintain the wall temperature well below the one required by the devices according to the prior art.

Finally, as the person skilled in the art can understand from the above comments, the heat exchange device 20 according to the invention is quite economical from a manufacturing point of view, being particularly suitable for use as a disposable insert or as a part of a disposable multifunction cassette. With regard to the embodiments of the device 20 and the thermal device 40 described above, the person skilled in the art may, in order to satisfy specific requirements, make modifications and/or replace elements described with equivalent elements, without thereby departing from the scope of the accompanying claims.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A device for providing a heat exchange with a medical liquid, said device comprising:
    an inlet that receives the medical liquid;
    an outlet that releases the medical liquid; and
    a duct that contains a flow of the medical liquid, the duct being enclosed between a first wall and a second wall, having a planar development defining a mean plane ($\pi$), and including an element that promotes turbulence in the flow of the medical liquid,
    with at least one of the first wall and the second wall being heated by a heat source so as to enable the heat exchange with the flow of the medical liquid, and
    with the element that promotes turbulence in the flow including a plurality of fins, with each fin of the plurality of fins having a lenticular cross section and defining a mean plane ($\tau_n$) substantially perpendicular to the mean plane ($\pi$) of the planar development,
    with the plurality of fins being arranged according to a repeating pattern (P) including four fins, with a first pair of the plurality of fins of the pattern (P) having mean planes ($\tau_1$, $\tau_3$) thereof parallel to one another, a second pair of the plurality of fins of the pattern (P) having mean planes ($\tau_2$, $\tau_4$) thereof parallel to one another, and with the mean planes ($\tau_1$, $\tau_3$) of the first pair of the plurality of fins being incident with the mean planes ($\tau_2$, $\tau_4$) of the second pair of the plurality of fins, and
    with the plurality of fins protruding inside the duct between the first wall and the second wall so as to induce the turbulence, provide for intense mixing in the flow of the medical liquid, and facilitate the heat exchange thereto.

2. The device according to claim 1, wherein the at least one of the first wall and the second wall configured to enable the heat exchange has a material of construction that is a metal, and has a thickness of between 0.1 mm and 0.4 mm.

3. The device according to claim 1, wherein the at least one of the first wall and the second wall configured to enable the heat exchange has a material of construction that is polymeric, and has a thickness of between 0.1 mm and 0.3 mm.

4. The device according to claim 1, wherein the element that promotes turbulence includes a continuous sheet from which the plurality of fins protrude on only one side thereof.

5. The device according to claim 1, wherein the element that promotes turbulence includes a discontinuous permeable sheet from which the plurality of fins protrude on both sides thereof.

6. The device according to claim 5, wherein the discontinuous permeable sheet includes holes at one end thereof and is partially permeable.

7. The device according to claim 1, wherein in the pattern (P) a distance between the mean planes of the first pair of the plurality of fins is equal to a distance between the mean planes of the second pair of the plurality of fins.

8. The device according to claim 1, wherein in the pattern (P) the mean planes of the first pair of the plurality of fins are perpendicular to the mean planes of the second pair of the plurality of fins.

9. The device according to claim 1, wherein in the pattern (P) intersections of the mean planes of the first pair of the plurality of fins and the mean planes of the second pair of the plurality of fins with the mean plane ($\tau$) define a quadrilateral ($Q_f$).

10. The device according to claim 9, wherein each of the plurality of fins protrudes from a side of the quadrilateral ($Q_f$) beyond a relative vertex.

11. The device according to claim 9, wherein the quadrilateral ($Q_f$) is a rhomb or a square.

12. The device according to claim 1, wherein in the pattern (P) a first mean plane ($\tau_1$) intersects a fourth fin, a second mean plane ($\tau_2$) intersects a first fin, a third mean plane ($\tau_3$) intersects a second fin, and a fourth mean plane ($\tau_4$) intersects a third fin.

13. The device according to claim 1, wherein in the pattern (P) a first mean plane ($\tau_1$) bisects a fourth fin, a second mean plane ($\tau_2$) bisects a first fin, a third mean plane ($\tau_3$) bisects a second fin, and a fourth mean plane ($\tau_4$) bisects a third fin.

14. The device according to claim 1, wherein the pattern (P) includes a plurality of pins.

15. The device according to claim 14, wherein the pattern (P) includes four of the plurality of pins.

16. The device according to claim 15, wherein in the pattern (P) the four pins are placed on vertices of a quadrilateral ($Q_p$) identical to a quadrilateral ($Q_f$) defined by the fins.

17. The device according to claim 16, wherein in the pattern (P) the quadrilateral ($Q_p$) and the quadrilateral ($Q_f$) partly overlap.

18. The device according to claim 17, wherein in the pattern (P) the quadrilateral ($Q_p$) and the quadrilateral ($Q_f$) overlap for a quarter of a surface of each of the quadrilateral ($Q_p$) and the quadrilateral ($Q_f$).

19. The device according to claim 16, wherein in the pattern (P), the quadrilateral ($Q_p$) surrounds one of the fins and the quadrilateral ($Q_f$) surrounds one of the pins.

20. The device according to claim 1, wherein the pattern (P) is arranged in the duct such that an overall liquid movement (M) is parallel to one of a diagonal of a quadrilateral ($Q_f$) defined by the fins.

21. An assembly comprising:
a device for providing a heat exchange with a medical liquid according to claim 1, and
the heat source, with the heat source being a thermally active element including a thermally active plate that contacts an outer side of the at least one of the first wall and the second wall which enable the heat exchange with the medical liquid in the duct.

22. The assembly according to claim 21, wherein the thermally active plate includes electric resistors or Peltier cells.

23. A disposable cassette for a peritoneal dialysis treatment or an automated peritoneal dialysis treatment, said disposable cassette comprising:
a polymeric structure defining a first part for pumping and distributing a medical liquid; and
a second part including a device for providing a heat exchange with the medical fluid,
the device including a duct that contains a flow of the medical liquid, the duct
being enclosed between a first wall and a second wall, with at least one of the first wall and the second wall being heated by a heat source so as to enable the heat exchange with the flow of the medical liquid,
having a planar development defining a mean plane ($\pi$), and including an element that promotes turbulence in the flow of the medical liquid,
with the element that promotes turbulence in the flow including a plurality of fins, with each fin of the plurality of fins having a lenticular cross section and defining a mean plane ($\tau_n$) substantially perpendicular to the mean plane ($\pi$) of the planar development,
with the plurality of fins being arranged according to a repeating pattern (P) including four fins, with a first pair of the plurality of fins of the pattern (P) having mean planes ($\tau_1$, $\tau_3$) thereof parallel to one another, a second pair of the plurality of fins of the pattern (P) having mean planes ($\tau_2$, $\tau_4$) thereof parallel to one another, and with the mean planes ($\tau_1$, $\tau_3$) of the first pair of the plurality of fins being incident with the mean planes ($\tau_2$, $\tau_4$) of the second pair of the plurality of fins, and
with the plurality of fins protruding inside the duct between the first wall and the second wall so as to induce the turbulence, provide for intense mixing in the flow of the medical liquid, and facilitate the heat exchange thereto.

24. An assembly comprising:
a disposable cassette according to claim 23; and
the heat source, with the heat source being a thermally active element including a thermally active plate that contacts an outer side of the at least one of the first wall and the second wall which enable the heat exchange with the medical liquid in the duct.

* * * * *